United States Patent [19]

Hart

[11] 4,254,073

[45] Mar. 3, 1981

[54] PYROPHOSPHONATES AND METHOD OF MAKING SAME

[75] Inventor: Vicki L. Hart, Jacksonville, Fla.

[73] Assignee: SCM Corporation, New York, N.Y.

[21] Appl. No.: 122,026

[22] Filed: Feb. 15, 1980

[51] Int. Cl.$^3$ .............................................. C07F 9/21
[52] U.S. Cl. ................... 260/927 R; 260/988
[58] Field of Search ........................... 260/988, 927 R

[56] References Cited

U.S. PATENT DOCUMENTS 4,183,879   1/1980   Battiste .................................. 260/932

*Primary Examiner*—Anton H. Sutto
*Attorney, Agent, or Firm*—Robert A. Sturges; Merton H. Douthitt

[57] ABSTRACT

A process for producing a novel intramolecular pyrophosphonate for example, dimethyl-p-menthane-2,7-diylpyrophosphonate by heating a diphosphonate for example, tetramethyl-p-menthane-2,7-diyldiphosphonate to a temperature between about 200° C. and 300° C. for a period from about 0.5 to about 10 hours, e.g., 6 hours.

19 Claims, No Drawings

PYROPHOSPHONATES AND METHOD OF MAKING SAME

This invention relates to new pyrophosphonates and a method for making them. More particularly, the invention relates to pyrophosphonates such as dialkyl para-menthan-2,7-diyl pyrophosphonate. The pyrophosphonates hereof are useful for treating inorganic pigments, e.g., $TiO_2$.

BACKGROUND OF THE INVENTION AND PRIOR ART

Intramolecular diphosphonic acids and esters of cycloalkanes, particularly para-menthane, have been disclosed in U.S. Ser. No. 924,165, now U.S. Pat. No. 4,183,879. In general, these compounds are prepared by reacting an unsaturated cyclohexyl material, or material convertible to a cyclohexyl material, such as alpha or beta-pinene, with a dialkyl hydrogen phosphite under effective free radical conditions. Because these prior materials are useful starting materials for making the novel pyrophosphonates hereof, the disclosure of said patent is included herein by reference thereto.

In other specific aspects, starting compounds for the present invention are conveniently prepared by adding a dialkyl hydrogen phosphite to a para-menthenephosphonate. This reaction is conducted under free radical conditions at temperatures of about 50° C. to about 200° C. for about 0.1 to 10.0 hours until the diphosphonate is formed. The precursor monophosphonate adducts can be prepared according to procedures reported by Kenney, et al., in *J. Org. Chem.*, Vol. 30., No. 5., pages 682–686 (1974) and by Francois, et al., in *C. R. Acad. Sci.*, Ser. C., Vol. 279., No. 3., pages 117–119 (1974).

Alternatively, diphosphonate, or diphosphonic acid ester starting materials for the present invention can be directly prepared by reacting unsaturated cyclohexyl materials such as beta-pinene, with a dialkyl hydrogen phosphite at a temperature in the range from 50° C. to 200° C. for a reaction time of from 0.1 to 10.0 hours, in the presence of a free radical initiator. A wide variety of conventional free radical initiators may be used. Typical free radical initiators are various peroxides, such as, ditertiary-butyl peroxide, hydrogen peroxide, benzoyl peroxide, and the like. Generally from about 0.1 to about 10 mole percent of the free radical initiator on the basis of the hydrocarbon is used in the reaction mixture.

Additionally, ultraviolet radiation may serve to establish the free radical conditions, including the situation when a UV photoinitiator is added to the reaction mixture. Atmospheric pressure is desired for use in producing the diphosphonates.

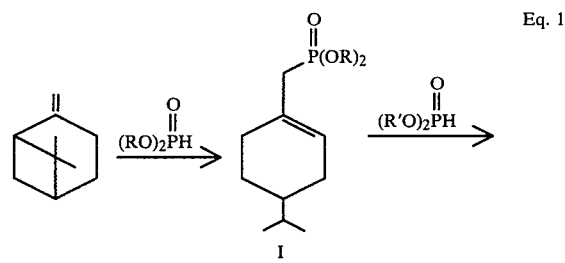

Eq. 1.

I

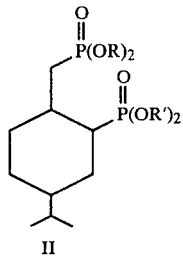

II

The pyrophosphonates of the present invention can be produced from diphosphonate esters such as those produced in accordance with the above U.S. Pat. No. 4,183,879 by heating at a temperature of from 200° C. to 300° C., preferably between 240° C. and 260° C. for a period of from 0.5 to 10 hours.

The closest known reference which has come to my attention is European Patent No. 00043 which discloses propane-1,3-dimethylphosphinic acid anhydride having the formula:

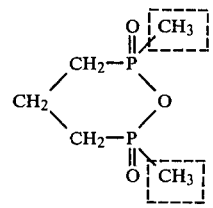

By contrast, in my novel compositions the radical attached to phosphorus and in the dotted area is alkoxy instead of alkyl, making the compositions phosphonates rather than phosphinates.

Another reference is the article by Gazizov, et al. in Zh. Obshch. Khim 1976, 46 (6), 1223–8, which discloses the reaction of dialkylchlorophosphites with acylals of acetic acid. This reaction gives a complex mixture of phosphorus-containing products whose structures are determined by spectroscopic and chromatographic methods. Thus, reaction of $(EtO)_2PCl$ with MeCH(OEt)OAc at 50° C. for 5 hrs. gave $(EtO)_2P(O)CHMeOEt$, $(EtO)_2P(O)Ac$ and $Cl(EtO)P(O)CHMeOEt$. Prolonged heating (~40 hr.) produces among other products $[CH_3CH(OEt)(EtO)P(O)]_2O$, a pyrophosphonate albeit an intermolecular one. It is significant that, according to the authors, this pyrophosphonate is not produced by direct thermal reaction of phosphonates as are the products of this invention.

Reference may also be made to U.S. Pat. No. 3,597,511 which discloses P-O-P compounds produced by reacting $P_2O_5$ with certain alkylene oxides.

French Pat. No. 1,281,973 discloses the preparation of certain aromatic pyrophosphates containing a P-O-P group. These again are not intramolecular pyrophosphonates.

BRIEF STATEMENT OF THE INVENTION

Briefly stated, the present invention is a process for producing a pyrophosphonate by intramolecular reaction of a diphosphonate. The process comprises heating a diphosphonate to a temperature between about 200° C. and 300° C. for a period from about 0.5 to 10 hours. These pyrophosphonates are particularly useful in the treatment of inorganic pigments such as titanium dioxide.

DETAILED DESCRIPTION OF THE INVENTION

The novel compounds of the present invention are considered to be intramolecular pyrophosphonates, in particular p-menthane-2,7-diylpyrophosphonates. By following known procedures such as indicated above, the diphosphonate precursors can be prepared. These particular diphosphonates, when heated at an elevated temperature in the range of 200° C.–300° C. for about 0.5 to 10 hours, yield an intramolecular pyrophosphonate. Beta-Pinene, for example, when converted to the diphosphonate in accordance with the process described by Battiste, yields on heating at 240° C.–260° C. a para-menthanepyrophosphonate. This result is particularly surprising in that the diphosphonate derived from alpha-pinene does not react similarly.

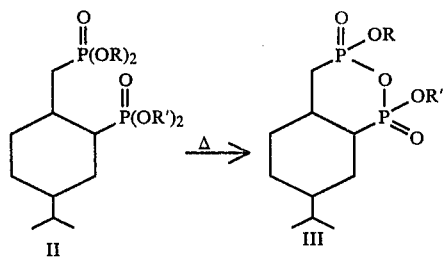

Eq. 2.

The novel compounds of the present invention may be represented by a structural formula as follows:

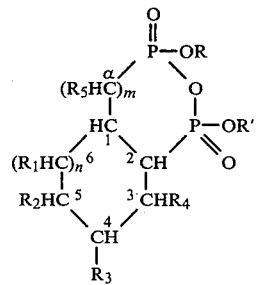

IV

Wherein m and n are independently selected from 0 and 1; R and R' are independently selected from $C_1$–$C_6$ alkyl groups, such as, methyl, ethyl, propyl, and isopropyl; n-butyl, sec-butyl, t-butyl, amyl, hexyl, cyclohexyl, phenyl and the like; and $R_1$, $R_2$, $R_3$, $R_4$ and $R_5$ are independently selected from hydrogen and $C_1$–$C_6$ hydrocarbyl groups, such as, methyl, ethyl, propyl, isopropyl, n-butyl, sec-butyl, tert-butyl, amyl, hexyl, cyclohexyl, phenyl, and the like. It will be observed that the novel compounds are characterized by the substructure:

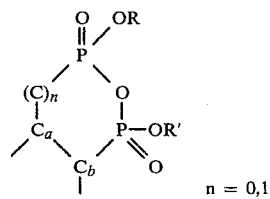

n = 0,1

We term this structure an intramolecular pyrophosphonate in contrast to an intermolecular pyrophosphonate in which carbon atoms a and b are not connected.

The following table gives specific examples of novel intramolecular pyrophosphonates of this invention: in this table the substituent groups are the R groups in the structural formula (IV) above.

TABLE I

| Ex. | R | R' | $R_1$ | $R_2$ | $R_3$ | $R_4$ | $R_5$ |
|---|---|---|---|---|---|---|---|
| 1 | $CH_3$ | $C_4H_9$ | H | H | H | H | H |
| 2 | $CH_3$ | $CH_3$ | H | H | H | H | H |
| 3 | $C_2H_5$ | $C_5H_{11}$ | H | H | H | H | H |
| 4 | $C_2H_5$ | $C_2H_5$ | H | H | H | H | H |
| 5 | **$C_3H_7$ | $C_6H_{13}$ | H | H | H | H | H |
| 6 | **$C_3H_7$ | Cyc-$C_6H_{11}$ | H | H | H | H | H |
| 7 | **$C_3H_7$ | **$C_3H_7$ | H | H | H | H | H |
| 8 | $CH_3$ | $CH_3$ | H | H | $CH_3$ | H | H |
| 9 | $CH_3$ | Cyc-$C_6H_{11}$ | H | H | **$C_3H_7$ | H | H |
| 10* | $CH_3$ | $CH_3$ | H | H | **$C_3H_7$ | H | H |
| 11 | $C_2H_5$ | $C_2H_5$ | H | H | **$C_3H_7$ | H | H |
| 12 | $CH_3$ | $CH_3$ | H | $CH_3$ | H | $CH_3$ | H |
| 13 | $CH_3$ | $CH_3$ | H | $C_2H_5$ | H | $C_2H_5$ | H |
| 14 | $CH_3$ | $CH_3$ | H | H | H | H | $CH_2$ |
| 15 | $CH_3$ | $CH_3$ | $CH_3$ | H | H | H | H |
| 16 | $CH_3$ | $CH_3$ | $CH_3$ | $CH_3$ | $CH_3$ | $CH_3$ | H |
| 17 | $CH_3$ | $CH_3$ | H | H | Cyc-$C_6H_{11}$ | H | H |
| 18 | $CH_3$ | $CH_3$ | H | H | phenyl | H | H |

*Example 10 represents the best mode.
**Iso-propyl

The various alkyl and aryl substituents in Table I may be introduced by known alkylation and arylation techniques.

The pyrophosphonates in Table I are prepared by heating the corresponding diphosphonates at an elevated temperature sufficient to evolve the ether, R-O-R'. Generally, 200°–300° C. will be found sufficient. The reaction is time-temperature related in the stated range, the higher temperatures requiring less time, the lower temperatures requiring more time. Generally, the reaction time is 0.5 to 10 hours.

The rate of reaction can be accelerated by the presence of catalytic amount of an acid such as phosphoric acid. It is recognized that suitable acids may be generated by partial hydrolysis of the phosphonates or pyrophosphonates involved in the reaction.

Tetramethyl p-menthane-2,7-diylphosphonate (V) is prepared according to Eq. 1. The new compound, i.e., the pyrophosphonate (VI) is obtained from (V) by heating it to a temperature between 240° and 260° C. for a period of from 0.5 to 10 hours. Formation of the pyrophosphonate is accompanied by evolution of dimethyl ether. NMR and mass spectrometer data are consistent with a compound of the structure (VI), which is formed according to Equation 3.

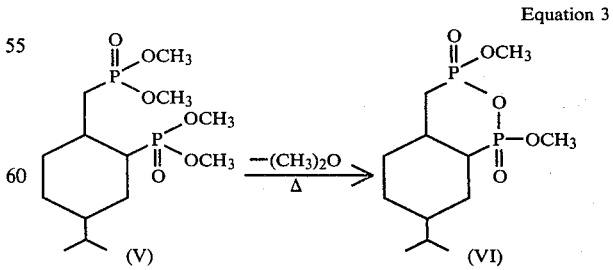

Equation 3

The product (VI) is soluble in acetone, tetrahydrofuran, diethyl ether, methylene chloride, and toluene.

As indicated above, it has been found that the novel pyrophosphonates of the present invention are useful for treating inorganic pigments, particularly opacifying inorganic or mineral pigments. A preferred example of an opacifying inorganic pigment beneficiated by the treatment is titanium dioxide. Specific examples of other inorganic pigments which may be beneficiated with the novel compounds of the present invention include clays, such as, kaolin; asbestos, calcium carbonate, zinc oxide, chromium oxide, barium sulfate, iron oxide, tin oxide, calcium sulfate, talc, mica, silicas, dolomite, zinc sulfide, antimony oxide, zirconium dioxide, silicon dioxide, cadmium sulfide, cadmium selenide, lead chromate, zinc chromate, nickel titanate, diatomaceous earth, glass fiber, glass powder, glass spheres, and the like, and mixtures thereof.

The titanium dioxide pigments include rutile and anatase titanium dioxides. These materials generally have an average particle size of less than 5000 Angstroms, and typically between 1000 and 5000 Angstroms. The inorganic pigment, e.g., $TiO_2$, is treated with the novel compound of the present invention by any suitable means such as by spraying a solution of the pyrophosphonate with the inorganic pigment followed by drying, or any other suitable technique, such as, disclosed in Weber, U.S. Pat. No. 4,209,430. The final treated pigment should retain sufficient proportion of the novel pyrophosphonate to provide an effective phosphorus content of at least about 0.02% by weight of the pigment. Conventional finishing operations may then be carried out on the treated inorganic pigment such as, for example, air or steam micronization of pigmentary $TiO_2$.

A significant pigmentary property improvement demonstrated by the treated $TiO_2$ pigments is suppression of yellowing when the treated pigment is dispersed in polyolefins, such as, polyethylene, polypropylene, etc., containing various phenolic antioxidants.

One manner of using the pyrophosphonates hereof is identical to that disclosed by Weber in U.S. Pat. No. 4,209,430, dated June 24, 1980, Ser. No. 963,301 filed Nov. 24, 1978 which discloses the treatment of inorganic pigments with diphosphonates, particularly diphosphonates produced in accordance with the disclosure of U.S. Pat. No. 4,183,879 to Battiste, Ser. No. 925,165 filed July 13, 1978.

The pyrophosphonate materials are also useful independently of pigmentary material as antiyellowing additives, i.e., stabilizers, in polyethylene and polypropylene. From about 0.1% to about 3% by weight of the pyrophosphonate in the polyene is effective to inhibit yellowing.

EXAMPLE 1

A flask was charged with 0.100 g of tetramethyl p-menthane-2,7-diyldiphosphonate and heated to 260° for a period of 6 hrs. Analysis of the product by mass spectrometry and nmr spectrometry showed over 90% conversion to dimethyl p-menthane-2,7-diylpyrophosphonate. Vapors from the reaction were collected and analyzed by mass spectroscopy to show the presence of substantial amounts of dimethyl ether.

EXAMPLE 2

The above reaction was repeated in the presence of 2 g of phosphoric acid. In the presence of the phosphoric acid catalyst, the reaction reached 90% conversion in 4 hrs. at 220°.

EXAMPLE 3

A 5.0 g portion of dimethyl p-menthane-2,7-diylpyrophosphonate was dissolved in 10 ml of methylene chloride and shaken with 10 ml of water. Analysis of the organic phase by nmr and mass spectroscopy showed total conversion to dimethyl p-menthane-2,7-diyldiphosphonate.

EXAMPLE 4

A solution of 5.0 g of dimethyl p-menthane-2,7-diylpyrophosphonate in 10 ml of methanol was heated to reflux for a period of 8 hrs. Methanol was then removed from solution under vacuum. Analysis of the product by nmr and mass spectroscopy showed about 90% conversion to trimethyl p-menthane-2,7-diyldiphosphonate.

In like manner, to Example 1, a dialkyl methylcyclohexane-2,α-diylpyrophosphonate is prepared by heating a tetraalkyl methylcyclohexane-2,α-diylphosphonate to a temperature between 200° and 300° C., e.g., 240° to 260° C., for from 0.5 to 10 hours and evolving dialkyl ether. Dialkyl cyclohexane-2,α-diylpyrophosphonates are prepared by heating the corresponding tetraalkyl cyclohexane-2,α-diylphosphonate to a temperature between 200° and 300° C., e.g., 240°–260° C., for from 0.5 to 10 hours and evolving dialkyl ether. Also, the cyclopentane analogues are similarly prepared by heating a tetraalkyl cyclopentane-2,α-diylphosphonate or tetraalkyl methyl cyclopentane-2,α-diylphosphonate to a temperature between 200° C. or 300° C., e.g., 240° to 260° C., for a period of 0.5 to 10 hours and evolving dialkyl ether. The alkyl groups attached to phosphorus atoms through oxygen are immaterial and may be the same or different, e.g., independently selected from methyl, ethyl, propyl, isopropyl, butyl, etc., up to 6 carbon atoms. Many other examples will occur to those skilled in the art and may be treated in the same manner to yield corresponding pyrophosphonates in accordance herewith.

What is claimed is:

1. An intramolecular pyrophosphonate having the formula:

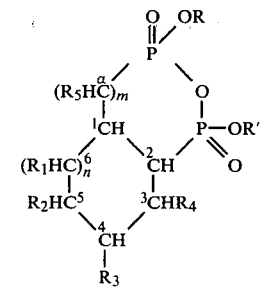

wherein n and m are independently selected from 0 and 1, R and R' are independently selected from $C_1$–$C_6$ alkyl groups and $R_1$, $R_2$, $R_3$, $R_4$ and $R_5$ are independently selected from hydrogen and $C_1$–$C_6$ hydrocarbyl groups.

2. A dialkyl methylcyclohexane-2,α-diylpyrophosphonate.

3. A dialkyl cyclohexane-1,2-diylpyrophosphonate.

4. A dialkyl methylcyclopentane-2,α-diylpyrophosphonate.

5. A dialkyl cyclopentane-1,2-diylpyrophosphonate.

6. A pyrophosphonate as defined in claim 1 in which m and n equal 1; $R_1$, $R_2$, $R_4$, and $R_5$ are H; and $R_3$ is isopropyl.

7. A pyrophosphonate as defined in claim 6 in which R and R' are each methyl.

8. A pyrophosphonate as defined in claim 6 in which R and R' are each ethyl.

9. A process for making an intramolecular pyrophosphonate having the formula:

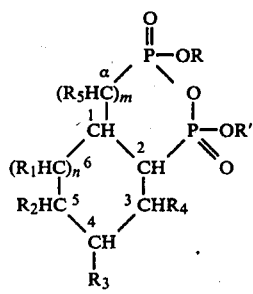

wherein m and n are independently selected from 0 and 1, R, R' are independently selected from $C_1$–$C_6$ alkyl groups and $R_1$, $R_2$, $R_3$, $R_4$ and $R_5$ are independently selected from hydrogen and $C_1$–$C_6$ hydrocarbyl groups, which comprises heating a diphosphonate having the formula:

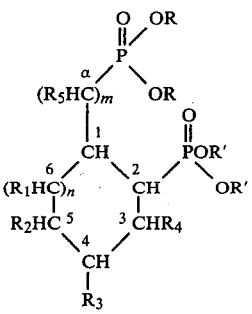

wherein m, n, R, R', $R_1$, $R_2$, $R_3$, $R_4$, and $R_5$ are defined as above, at a temperature in the range of 200°–300° C. for a period of from 0.5 to 10 hours.

10. A process for making a dialkyl methylcyclohexane-2,α-diylpyrophosphonate which comprises heating a tetraalkyl methylcyclohexane-2,α-diyldiphosphonate to a temperature of from 200°–300° C. for from 0.5 to 10 hours.

11. A process for making a dialkyl cyclohexane-1,2-diylpyrophosphonate which comprises heating a tetraalkyl cyclohexane-1,2-diyldiphosphonate to a temperature of from 200°–300° C. for from 0.5 to 10 hours.

12. A process for making a dialkyl methylcyclopentane-2,α-diylpyrophosphonate which comprises heating a tetraalkyl methylcyclopentane-2,α-diyldiphosphonate to a temperature of from 200°–300° C. for from 0.5 to 10 hours.

13. A process for making a dialkyl cyclopentane-1,2-diylpyrophosphonate which comprises heating a tetraalkyl cyclopentane-1,2-diyldiphosphonate to a temperature of from 200°–300° C. for from 0.5 to 10 hours.

14. A process as defined in claim 9 wherein m and n equal 1, $R_1$ is H, and $R_3$ is a 1 to 6 carbon atom hydrocarbyl group.

15. A process as defined in claim 14 wherein $R_3$ contains three carbon atoms.

16. A process as defined in claim 15 wherein the $R_3$ is isopropyl.

17. A process as defined in claim 9 wherein m and n equal 1, $R_1$, $R_2$, $R_4$, and $R_5$ are H and $R_3$ is isopropyl.

18. A process as defined in claim 17 wherein R and R' are each methyl.

19. A process as defined in claim 17 where R and R' are each ethyl.

* * * * *